(12) United States Patent
Buckingham et al.

(10) Patent No.: US 8,049,636 B2
(45) Date of Patent: Nov. 1, 2011

(54) SYSTEM, METHODS AND APPARATUS FOR MONITORING VIA A HAND HELD TOOL

(75) Inventors: Mark-Paul Buckingham, Edinburgh (GB); John Paul McKeown, Edinburgh (GB); Tim Kent, Edinburgh (GB); Charles Keepax, Edinburgh (GB); Stephen Dickson, Edinburgh (GB); Donald Black, Edinburgh (GB)

(73) Assignee: Reactec Limited, Edinburgh (GB)

( * ) Notice: Subject to any disclaimer, the term of this patent is extended or adjusted under 35 U.S.C. 154(b) by 392 days.

(21) Appl. No.: 12/158,512

(22) PCT Filed: Dec. 22, 2006

(86) PCT No.: PCT/GB2006/004939
§ 371 (c)(1),
(2), (4) Date: Oct. 23, 2008

(87) PCT Pub. No.: WO2007/072068
PCT Pub. Date: Jun. 28, 2007

(65) Prior Publication Data
US 2009/0091465 A1 Apr. 9, 2009

(30) Foreign Application Priority Data
Dec. 23, 2005 (GB) .................................. 0526363.7
Mar. 14, 2006 (GB) .................................. 0605090.0

(51) Int. Cl.
*G08B 21/00* (2006.01)
*G08B 23/00* (2006.01)
(52) U.S. Cl. ..... 340/683; 340/679; 340/680; 340/572.1; 340/693.5; 340/693.9
(58) Field of Classification Search .................. 340/679, 340/680, 683
See application file for complete search history.

(56) References Cited

U.S. PATENT DOCUMENTS
4,758,964 A 7/1988 Bittner et al.
(Continued)

FOREIGN PATENT DOCUMENTS
DE 101 19 252 11/2002
(Continued)

OTHER PUBLICATIONS

Type 2239 B, Hand-Arm Vibration and Integrating Sound Level Meter, Hand-Arm Vibration Functions, Dec. 2001, XP002465289, Retrieved from the Internet: URL: http://www.bksv.nl/tbDoc/3761/Handleiding%202239B.pdf>, 4 pages.

(Continued)

*Primary Examiner* — Julie Lieu
(74) *Attorney, Agent, or Firm* — John D. Lanza; Foley & Lardner LLP

(57) ABSTRACT

The present invention relates to hand held tool monitoring apparatus (10). The hand held tool monitoring apparatus (10) comprises a mount, which in use of the hand held tool monitoring apparatus forms part of a hand held tool (22), and a monitoring component (12) configured to be releasably attached to the mount. The monitoring component (12) comprises an operative part of the hand held tool monitoring apparatus (10) and the hand held tool monitoring apparatus further comprises a vibration sensor and a timer. The vibration sensor is operable to sense vibration of the hand held tool (22) and to provide a vibration signal in response to sensed vibration when the monitoring component is attached to the mount. The timer is operative in dependence on the vibration signal to record a duration of vibration of the hand held tool (22).

18 Claims, 7 Drawing Sheets

U.S. PATENT DOCUMENTS

| | | | |
|---|---|---|---|
| 4,827,771 A | | 5/1989 | Cary et al. |
| 5,257,199 A * | | 10/1993 | Tsujino et al. ............... 700/160 |
| 5,396,801 A | | 3/1995 | Komura |
| 5,587,931 A * | | 12/1996 | Jones et al. .................... 702/34 |
| 6,111,515 A * | | 8/2000 | Schaer et al. ................. 340/680 |
| 6,434,507 B1 * | | 8/2002 | Clayton et al. ............... 702/152 |
| 6,490,929 B1 | | 12/2002 | Russell et al. |
| 6,490,930 B1 | | 12/2002 | Ohkubo et al. |
| 7,613,590 B2 * | | 11/2009 | Brown ......................... 702/188 |
| 7,850,071 B2 * | | 12/2010 | Sakamoto et al. ............ 235/376 |
| 2004/0183689 A1 * | | 9/2004 | Luebke et al. ................ 340/680 |
| 2005/0000998 A1 | | 1/2005 | Grazioli et al. |
| 2005/0087019 A1 * | | 4/2005 | Face ................................ 73/649 |
| 2005/0128083 A1 | | 6/2005 | Puzio et al. |
| 2005/0177333 A1 | | 8/2005 | Lindberg et al. |
| 2006/0074513 A1 * | | 4/2006 | DeRose et al. ............... 700/175 |
| 2007/0008162 A1 * | | 1/2007 | Gossett et al. ................ 340/680 |
| 2009/0040061 A1 * | | 2/2009 | Golunski et al. ............. 340/683 |

FOREIGN PATENT DOCUMENTS

| | | |
|---|---|---|
| GB | 2 299 168 A | 9/1996 |
| GB | 2299169 | 9/1996 |
| GB | 2 321 109 A | 7/1998 |
| GB | 2 411 472 A | 8/2005 |
| GB | 2 413 189 A | 10/2005 |
| SU | 1740993 | 6/1992 |
| WO | WO-00/73999 A1 | 12/2000 |
| WO | WO 2005120348 | 12/2005 |

OTHER PUBLICATIONS

International Search Report dated Jun. 19, 2008 for WO 2007/072068, 79 pages.

Written Opinion of the International Search Authority dated Jun. 23, 2008 for WO 2007/072068, 9 pages.

International Prelimina Resort on Patentability dated Jun. 24, 2008 for WO 2007/072068, 10 pages.

Examiner's First Examination Report dated Oct. 22, 2008 for EP 0683149.5, 3 pages.

Examiner's Second Examination Report dated Nov. 5, 2010, for EP 0683149.5, 3 pages.

"Industrial Hygiene Vibration Monitor Model IHVM 100," Larson Davis. 4 pages.

"Vibration Monitoring." Industrial Safety & Hygiene News 38.11 (2004): p. 42 (ABSTRACT).

"Vibration Monitors & Real-Time Vibration Analyzers," Quest. 6 pages.

Bendel, Karl, Martin Fischer, and Matthias Schussler. "Vibrational Analysis of Power Tools Using a Novel Three Dimensional Scanning Vibrometer." Proc SPiE Int Opt Eng 5503 (2004): pp. 177-184 (ABSTRACT).

Gurram, R., S. Rakheja, and Gerard J. Gouw. "Vibration Transmission Characteristics of the Human Hand-arm and Gloves." International Journal of Industrial Ergonomics 13.3 (1994): pp. 217-234 (ABSRACT).

Hudock, Stephen D. "Hand-arm Vibration in a Group of Hand-operated Grinding Tools." Hum Fact Ergon Manuf 12 (2002): pp. 211-226 (ABSTRACT).

Rossi, G.L., and E.P. Tomasini. "Hand-arm Vibration Measurement by a Laser Scanning Vibrometer." Measurement: Journal of the International Measurement Confederation 16 (1995): pp. 113-124 (ABSTRACT).

Schenk et al. "Mechanism for the personbound measurement of characteristic values ofthe hand poor in and complete body oscillation load jobs (oscillation dosimeters)." Abstract of Patent No. DE-101 19 252 published Nov. 21, 2002.

* cited by examiner

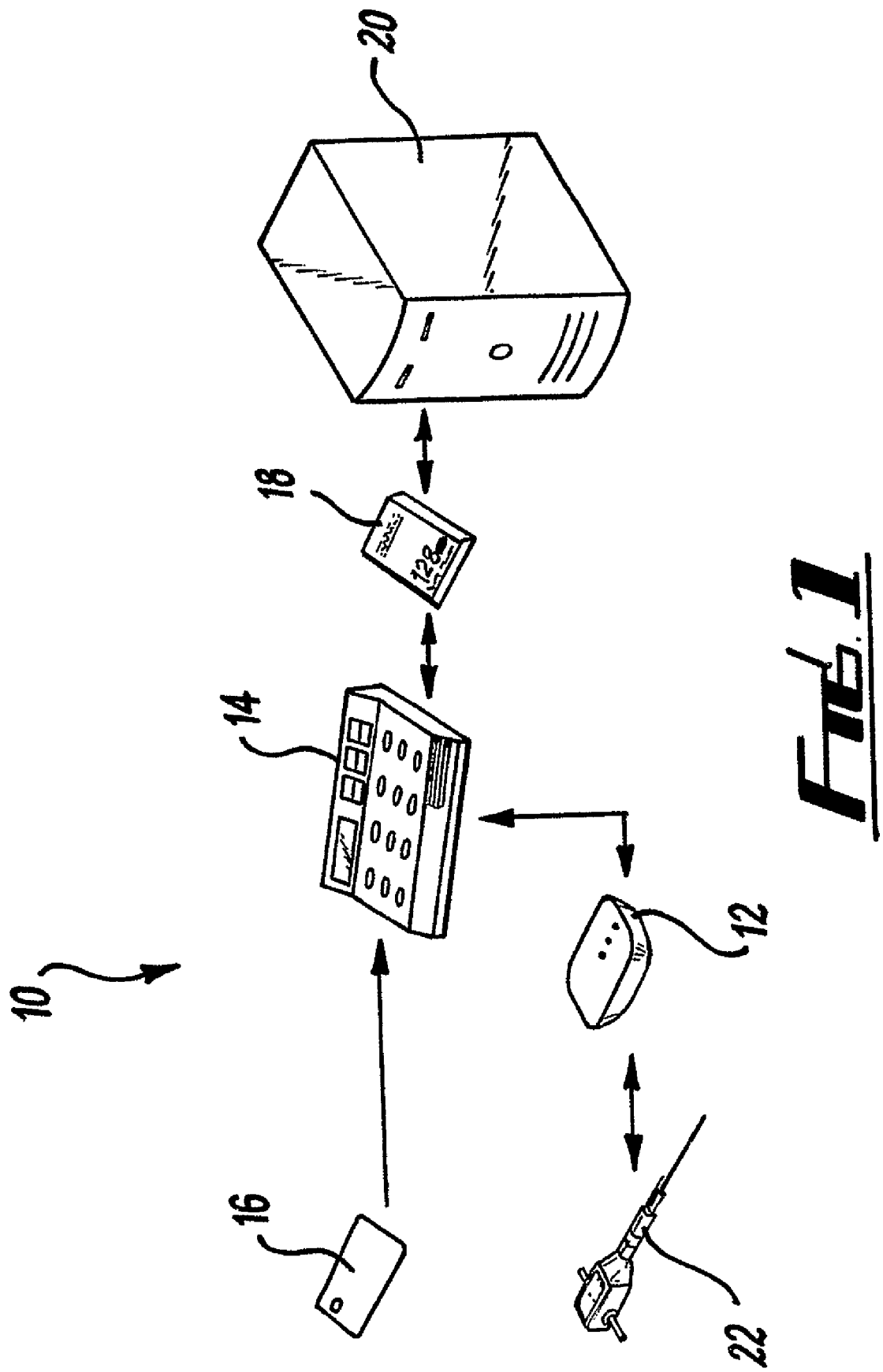

SYSTEM, METHODS AND APPARATUS FOR MONITORING VIA A HAND HELD TOOL

FIELD OF THE INVENTION

The present invention relates to a monitoring apparatus and method and in particular a hand held tool monitoring apparatus and method.

BACKGROUND TO THE INVENTION

Many hand held or hand guided tools transmit vibration to the hands and arms of the operator. It is known that such transmitted vibration, which is often termed Hand Arm Vibration (HAV), can cause painful and disabling diseases, such as white finger, following regular long term exposure.

Apparatus for monitoring exposure to HAV inducing tools is known. GB 2411472A describes a vibration monitor that is worn by the operator. The vibration monitor of GB 2411472A comprises a vibration sensor and memory. The vibration sensor measures the magnitude and frequency of vibration of a tool being used by the operator, the magnitude and frequency of vibration being stored in the memory along with a time and date stamp. GB 2413189A describes a vibration monitor that is held by an operator. The vibration monitor comprises a vibration sensor and processing electronics. The vibration sensor measures the vibration of a tool being used by the operator and the processing electronics determines the operator's cumulative exposure to the vibration and provides an indication to the operator before exposure to the vibration exceeds a safe level. GB 2299168A describes a vibration monitor that is worn on the wrist of an operator. The vibration monitor comprises a vibration sensor and processing electronics. The vibration sensor measures vibrations experienced by the operator during use of a tool and the processing electronics operates an alarm when an accumulated time that the vibration level exceeds a predetermined threshold exceeds a predetermined duration.

The present inventor has appreciated that the above described apparatus have disadvantages.

It is therefore an object of the present invention to provide apparatus for measuring vibration of a hand held tool.

It is a further object of the present invention to provide apparatus for measuring a duration of vibration of a hand held tool.

STATEMENT OF INVENTION

The present invention has been devised in the light of the above noted appreciation and thus from a first aspect there is provided hand held tool monitoring apparatus comprising a mount, which in use of the hand held tool monitoring apparatus forms part of a hand held tool, and a monitoring component configured to be releasably attached to the mount, the monitoring component comprising an operative part of the hand held tool monitoring apparatus, the hand held tool monitoring apparatus further comprising a vibration sensor and a timer, the vibration sensor being operable to sense vibration of the hand held tool and provide a vibration signal in response to sensed vibration when the monitoring component is attached to the mount, and the timer being operative in dependence on the vibration signal to record a duration of vibration of the hand held tool.

In use, the monitoring component is either attached to the mount on the hand held tool or forms part of the hand held tool and the hand held tool is operated. Vibration produced by the hand held tool is sensed by the vibration sensor and the timer is operative in dependence thereon to record a duration of the vibration. When use of the tool is complete, the monitoring component can be removed from the mount. Thus, the monitoring component can, for example, be used by an operator on another hand held tool. The inventors have appreciated that measuring vibrations directly on the tool, in contrast to GB 2411472A, GB 2413189A and GB 2299168A, can provide for more accurate and reliable measurement of vibration experienced by the operator. More specifically, the accuracy and reliability of the apparatus of GB 2411472A, GB 2413189A and GB 2299168A can depend on how the apparatus is used. For example, if a tool is gripped with a hand other than the hand or arm supporting the known apparatus, the vibration level or duration may not be measured properly. Furthermore, measurement of vibration by the known apparatus is affected by where the apparatus is worn or how the apparatus is held. As the vibration sensor forms part of either the mount or the monitoring component, which, in use, is attached to a hand held tool to be monitored, the present invention involves measurement of vibration directly on the hand held tool and yet provides for removal of the monitoring component from the tool. Thus, the monitoring component can be used, for example, to provide a record of vibration exposure for a particular operator.

More specifically, the monitoring component may be configured to be carried by an operator.

More specifically, the monitoring component may be of a size that permits the monitoring component to be received in a pocket of an operator.

Alternatively or in addition, the monitoring component may be configured for use by a particular operator. For example, the monitoring component may comprise a code, perhaps in electronic form, identifying the monitoring component as being for use with the particular operator.

Alternatively or in addition, the mount may be configured to be attached to the hand held tool. For example, the mount may be attached by means of bolts, rivets or similar such means that provides for permanent attachment of the mount to the tool.

Alternatively or in addition, the mount may form an integral part of the hand held tool. For example, the mount enclosure may be integrally formed with a casing of the hand held tool.

More specifically, the hand held tool and the hand held tool monitoring apparatus may be configured to switch off the hand held tool when a predetermined condition is satisfied.

More specifically, the hand held tool and the hand held tool monitoring apparatus may be configured to switch off the hand held tool by stopping supply of power to operate the hand held tool.

Alternatively or in addition, the predetermined condition may comprise at least one of: a vibration level value being reached; and an incorrect license being provided for the hand held tool monitoring apparatus. In the case of a vibration value being reached, the predetermined condition may be satisfied when a vibration level or recorded duration of vibration exceeds a predetermined threshold, such as a threshold indicative of a vibration dose level being exceeded. In the case of an incorrect license being provided, a user may have to enter identification information to the monitoring component identifying him as the user of the monitoring component and, hence, of the hand held tool. The provision of a check on the license can reduce the likelihood of an unauthorised person using the hand held tool or the likelihood of a person whose vibration dosage rate has been exceeded using the hand held tool.

Alternatively or in addition, the mount and monitoring component may be configured to be detached from each other by a single manual operation by a user. For example, the monitoring component may be separated from the mount by the user pulling the monitoring component away from the mount or twisting the monitoring component in relation to the mount.

Alternatively or in addition, the monitoring component and the mount may comprise respective cooperating magnetic components that in use provide for releasable attachment of the monitoring component to the mount. Thus, the monitoring component may be detached rapidly from the mount by a user.

Alternatively or in addition, the monitoring component and the mount may have respective surface profiles configured to engage with each other to provide for releasable attachment of the monitoring component to the mount.

More specifically, the mount may define a recess configured to receive at least a part of a body of the monitoring component.

Alternatively or in addition, the monitoring component may comprise a power switch that is configured to switch on the monitoring component when the monitoring component is attached to the mount.

More specifically, the power switch may comprise at least one of: an electrically actuated switch; and a mechanically actuated switch. The electrically actuated switch may be magnetically actuated. For example, electrically actuated switch may be a reed switch. The mechanically actuated switch may be a push button switch. Thus, where a push button switch is used, the monitoring apparatus may be configured such that attaching the monitoring component to the mount actuates the push button switch.

Alternatively or in addition, the mount may comprise hand held tool information for the hand held tool to which the mount is attached.

More specifically, the mount may be configured to convey the hand held tool information to the monitoring component.

More specifically, the mount may comprise a communications component operable to wirelessly convey the hand held tool information to the monitoring component.

More specifically, the communications component may be passive. For example, the communications component may be an RFID tag.

More specifically, the monitoring component may be operable to actuate the passive communications component and receive hand held tool information conveyed from the mount.

Alternatively or in addition, the hand held tool information may comprise hand held tool identification information. Such identification information may, for example, be a serial code for the hand held tool to which the mount is attached.

Alternatively or in addition, the hand held tool information may comprise hand held tool vibration information.

More specifically, the hand held tool vibration information may comprise a predetermined vibration dosage rate. The vibration dosage rate may be a value of vibration created by the hand held tool when in use over a predetermined period of time. The vibration dosage rate may be predetermined on the basis of a manufacturer's specification or on the basis of measurements made on the hand held tool, e.g. at the location of the trigger handle on the hand held tool.

Alternatively or in addition, where the vibration sensor is configured to be responsive to vibrations in three mutually orthogonal axes the hand held tool vibration information may comprise vibration axis information regarding which measurement axis or combination of axes is be used for measurement or detection of vibrations.

Alternatively or in addition, the monitoring component may be configured to provide a vibration exposure value in dependence upon the vibration dosage rate conveyed from the mount and the duration of vibration recorded by the timer.

More specifically, the monitoring component may be configured to multiply the vibration dosage rate by the duration of vibration recorded by the timer to provide a vibration exposure value.

Alternatively or in addition, the vibration sensor may comprise at least one vibration sensor, such as at least one tri-axial accelerometer.

More specifically, the vibration sensor may comprise a plurality of vibration sensors.

Alternatively or in addition, the monitoring apparatus may be configured to be operative in dependence upon at least one of a plurality of vibration signals.

More specifically, the monitoring apparatus may be configured to be operative in dependence upon a selected one of the plurality of vibration signals. For example, the plurality of vibration signals may differ from each other as regards a particular characteristic, such as range of detectable acceleration, sensitivity, noise, range of vibration frequency or axis of vibration.

In a form, the vibration sensor may be configured to be responsive to a plurality of ranges of detectable acceleration and to provide a vibration signal for each range. Thus, the monitoring apparatus may be configured to select a vibration signal of greatest amplitude from the plurality of vibration signals. For example, where the vibration sensor comprises three accelerometers with a first accelerometer tuned to be responsive to a low level of maximum acceleration, a second accelerometer tuned to be responsive to a medium level of maximum acceleration and a third accelerometer tuned to be responsive to a high level of maximum acceleration, the vibration signal of greatest amplitude can be selected.

In another form, the vibration sensor may be configured to be responsive to vibrations in three mutually orthogonal axes and to provide a vibration signal for each axis.

More specifically, the monitoring apparatus may be configured to select one of the three vibration signals.

More specifically, the monitoring apparatus may be operative to select a vibration signal on the basis of a comparison amongst the three vibration signals, e.g. to select a vibration signal of highest value representative of a strongest vibration.

Alternatively or in addition, a root mean square (RMS) value of a vibration signal may be taken. Where there is more than one vibration sensor a root mean square value of a vibration signal from each vibration sensor may be taken.

Alternatively or in addition, the monitoring apparatus may be configured to operate the timer in dependence upon the selected one of the vibration signals.

Alternatively or in addition, the monitoring component may be configured to provide for accumulated storage of data, such as vibration exposure values. Thus an exposure value can be accumulated over an extended period of time, e.g. over a whole day when the tool is used several times during the day.

Alternatively or in addition, the hand held tool vibration information may comprise a predetermined vibration threshold value. The vibration threshold value may be representative of a minimum level of vibration exhibited when the hand held tool is operating and ready for use. The vibration threshold value can be employed to distinguish between vibration levels when the hand held tool is operating and ready for use and vibration levels when the tool is in stand-by but not operating and ready for use. For example non-electrically or non-pneumatically powered tools, such as combustion engine driven tools, have a lower but significant level of vibration when they are connected to a source of power and switched on and in stand-by (i.e. when the internal combustion engine is running) than when they are operating and ready for use (e.g. when the blades of a hedge cutter are operating). Likewise, certain electrically or pneumatically powered tools may be intended to operate and be ready for use for only a proportion of the time that they are switched on. Thus, such electrically or pneumatically powered tools, e.g. an angle grinder, may have a vibration threshold value representative of a minimum level of vibration reached when the tool is operating and ready for use (e.g. when the disc of the angle grinder is rotating).

Thus, the monitoring component may be configured to operate the timer in dependence upon the vibration threshold value. More specifically, the monitoring component may be operative to compare the vibration signal provided by the vibration sensor with the vibration threshold value and to operate the timer in dependence upon the comparison. Thus, if the vibration signal is greater than the vibration threshold value the timer may be started. Also, if the vibration signal falls below the vibration threshold value the timer may be stopped.

More specifically, where the vibration sensor is configured to be responsive to vibrations in three mutually orthogonal axes and to provide a vibration signal for each axis and the hand held tool vibration information comprises vibration axis information, the monitoring component may be operative to select a vibration signal or a combination of vibration signals on the basis of the vibration axis information.

Alternatively or in addition, where the vibration sensor is configured to be responsive to vibrations in three mutually orthogonal axes and to provide a vibration signal for each axis, the monitoring component may be operative to select a vibration signal or a combination of vibration signals based on a comparison amongst the three vibration signals and to use the selected vibration signal or signals in the comparison with the vibration threshold value.

More specifically, the monitoring component may be operative to select a vibration signal or a combination of vibration signals that is representative of a strongest vibration.

The hand tool monitoring apparatus may further comprise an indicator configured to indicate at least one vibration value in dependence on the vibration signal.

More specifically, the at least one indicated vibration value may comprise at least one vibration exposure value.

More specifically, the at least one vibration exposure value may comprise a remaining exposure value for the current day of use of the monitoring apparatus by a user. There may be a safe daily vibration exposure limit for a user. Thus, the remaining exposure value can provide a useful indication of how much further work can be done by the user before his exposure limit is reached.

Alternatively or in addition, the at least one vibration exposure value may comprise a user's accumulated exposure value over a plurality of uses. Thus, for example, where a user attaches the monitoring apparatus to a particular tool and makes use of the monitoring apparatus in the morning, then detaches the monitoring apparatus for a period of time before re-attaching the monitoring apparatus to the particular tool for re-use in the afternoon, the accumulated exposure value corresponds to the sum of exposure values during the morning and afternoon uses of the monitoring apparatus.

Alternatively or in addition, the at least one vibration exposure value may comprise a user's last exposure value during use of the monitoring apparatus with a most recently used tool. Thus, for example, where the monitoring apparatus is used with several tools in turn the last exposure value corresponds to the exposure value measured during use with the most recently used tool.

Alternatively or in addition, the indicator may comprise a plurality of digits operative to display the at least one vibration exposure value.

More specifically, where the at least one vibration exposure value comprises a remaining exposure value for the current day of use, an accumulated exposure value, and a last exposure value, the indicator may be operative to display at least two of these exposure values simultaneously.

Alternatively, the indicator may be operative to display at least two of the exposure values on an alternating basis.

Alternatively or in addition, the indicator may be operative to display the remaining exposure value alternatively with either the accumulated exposure value or the last exposure value.

More specifically, the monitoring apparatus may be operative to select the accumulated exposure value for display when the monitoring apparatus is attached to a tool.

Alternatively, the monitoring apparatus may be operative to select the last exposure value for display when the monitoring apparatus is detached from a tool.

Alternatively or in addition, the indicator may be configured to indicate a plurality of categories of vibration value.

More specifically, the indicator may comprise a plurality of visual indicators, each visual indicator being operative to indicate one of the plurality of categories of vibration value, e.g. corresponding to a vibration level being below a warning level value, a vibration level being above the warning level value and a vibration level being above a exposure limit value.

More specifically, the visual indicators may be operative to display different colours, e.g. green, amber and red.

In a first form the monitoring component may comprise the vibration sensor and the timer.

In a second form the mount may comprise the vibration sensor and the monitoring component may comprise the timer. The monitoring component may comprise a microprocessor. Thus, the timer may be comprised as part of the microprocessor.

In a third form the mount may comprise the vibration sensor and the timer. More specifically, the monitoring component may comprise a data storage memory.

More specifically, the monitoring component may be configured to periodically store a vibration based on the vibration signal in the data storage memory. Thus, a record of vibration levels during use can be made. For example, the monitoring component may be constituted as an active RFID card.

The hand tool monitoring apparatus may further comprise a user identification component configured to identify one of a plurality of possible users. This can be advantageous, for example, where the hand tool monitoring apparatus is used in a place of employment and is liable to use by any one of a number of employees.

More specifically, the user identification component may comprise a specific user component (e.g. a magnetic strip identification card) comprising information for a specific user (e.g. the specific user's payroll number) and configured to be carried by the specific user; and a separate, specific user configurable component associated with the vibration sensor and to which information for the specific user can be conveyed. In use, a user can carry the specific user component and use it to convey information specific to him to the user configurable component. This allows the hand tool monitoring apparatus to be used by several users. More specifically, use of the tool by different users can be distinguished and a vibration exposure for each user can be determined.

The hand tool monitoring apparatus may further comprise a base component configured for use at a central location spaced apart from a location of use of the vibration sensor on a hand held tool.

More specifically, the base component and the vibration sensor may be configured for transmission of a transmission signal between the base component and the vibration sensor.

More specifically, the base component and the vibration sensor may be configured for transmission of the transmission signal by at least one of a wired coupling and an inductive coupling.

Alternatively or in addition, the transmission signal may comprise at least one of a power signal, e.g. for recharging a battery in the vibration sensor, and a data signal. Thus, in a preferred form a battery of the vibration sensor may be re-charged by way of an inductive coupling between the base component and the vibration sensor.

Alternatively or in addition, the base component may be configured to provide for at least one of: storage of the vibration sensor when not in use; re-charging of a battery power supply associated with the vibration sensor; storage of data recorded in use of the vibration sensor on a hand held tool; and configuring of a vibration sensor for use by a specific user by means of specific user information.

More specifically, the base component may be configured for use with a plurality of vibration sensors.

Alternatively or in addition, the operative part of the hand held tool monitoring apparatus may comprise at least one of: the vibration sensor, the timer and data storage memory.

Alternatively or in addition, the monitoring apparatus may further comprise communications apparatus comprising first and second Radio Frequency Identification (RFID) transceivers, the first and second RFID transceivers being configured to wirelessly transmit data between the first and second RFID transceivers, the first RFID transceiver forming part of the base component and the second RFID transceiver forming part of the monitoring component.

More specifically, the first and second RFID transceivers may be configured for operation at least one of: 125 kHz and 13.56 MHz.

Alternatively or in addition, one of the first and the second RFID transceivers may be configured by having its emanated RF field turned off. Thus, of the two RFID transceivers only one may have its emanated field turned on, namely the RFID transceiver that is transmitting data.

More specifically, where the RFID transceivers are operable at 125 kHz, the emanated field may be turned off by writing an appropriate command to the RFID transceiver.

Alternatively, where the RFID transceivers are operable at 13.56 MHz, the emanated field may be turned off by writing a series of '1's to the RFID transceiver after a control word containing option bits is written to the RFID transceiver.

Alternatively or in addition, the first and second RFID transceivers may be configured for handshaking between them before transmission of data from one to the other.

More specifically, the base component may comprise an RFID transponder and the second RFID transceiver may be configured to receive data from the RFID transponder. When the second RFID transceiver receives data from the RFID transponder, the second RFID transceiver may be configured to wait for the first RFID transceiver to transmit data.

Alternatively or in addition, the first and second RFID transceivers may be configured for duplex transmission of data between them.

Alternatively or in addition, the hand held tool monitoring apparatus may further comprise an isolator operative to change the vibration signal to take account of a change in a vibration characteristic between the hand held tool and the operator. Thus, the isolator may, for example, be used to take account of the vibration reducing effects of an isolated handle on the hand held tool.

More specifically, the isolator may comprise at least one filter. More specifically, the filter may comprise at least one of: an electronic filter; and a mechanical filter (e.g. rubber provided underneath the vibration sensor). An electronic filter may, for example, be provided for each axis of vibration. Where the filter is an electronic filter, filter coefficients may be predetermined and stored, for example, in the mount.

Alternatively or in addition, the hand held tool monitoring apparatus may be operative to store the vibration signal. Thus, the vibration signal may be used to, for example, provide an indication of incorrect use of a tool as indicated by an abnormally high level of vibration. Alternatively the vibration signal may be used, for example, to provide an indication (e.g. in terms of an abnormally high level of vibration or a particular frequency characteristic) of a fault with the tool or a need to have the tool serviced. The vibration signal may also be used to provide a check of a vibration exposure determined on the basis of operation of the timer.

Alternatively or in addition, the hand held tool monitoring apparatus may be configured to store data (e.g. recorded durations of vibration) that is at least one of: time stamped and date stamped. Thus, a record may be established of vibration dosage over a period of time.

The term hand held tool as used herein is to be construed as covering hand guided tools and indeed any kind of tool or machine that during use is in contact with an operator's hand or other part of his body.

Further embodiments of the above aspect may comprise one or more features of the following aspects.

According to a second aspect of the present invention there is provided a hand held tool monitoring method using monitoring apparatus comprising a mount and a monitoring component, the method comprising the steps of: attaching the monitoring component, which comprises an operative part of the hand held tool monitoring apparatus, to the mount, the mount, in use, forming part of the hand held tool, the monitoring component and mount being configured for releasable attachment of the monitoring component to the mount; operating a vibration sensor of the hand held tool monitoring apparatus to sense a vibration of the hand held tool and to provide a vibration signal in dependence upon the sensed vibration; operating a timer of the hand held tool monitoring apparatus in dependence upon the vibration signal to record a duration of vibration of the hand held tool; and removing the monitoring component from the mount.

More specifically, the step of attaching the mount to the hand held tool may comprise attaching the mount at a location on the hand held tool spaced apart from a location where an operator engages the hand held tool when the tool is in use.

More specifically, the step of attaching the mount to the hand held tool may comprises attaching the mount at a location on the hand held tool that is as close as is practical to a location where an operator engages the hand held tool when the tool is in use.

Embodiments of the second aspect of the present invention may comprise one or more features of the first aspect of the present invention.

According to a third aspect of the present invention there is provided a hand held tool comprising hand held tool monitoring apparatus according to the first aspect of the present invention.

Embodiments of the third aspect of the present invention may comprise one or more features of the first aspect of the present invention.

According to a fourth aspect of the present invention, there is provided a hand held tool monitoring apparatus comprising a vibration sensor and a timer, the vibration sensor in use forming part of a hand held tool and being operable to sense vibration of the hand held tool and provide a vibration signal in response to sensed vibration, the timer being operative in dependence on the vibration signal to record information corresponding to a duration of vibration of the hand held tool, the hand held tool monitoring apparatus being operative to store information corresponding to the vibration signal.

More specifically, the hand held tool monitoring apparatus may further comprise a data store.

More specifically, the data store may be operative to store information corresponding to the vibration signal and a duration recorded by the timer.

Alternatively or in addition, the vibration sensor may form part of a mount.

More specifically, the mount may be configured to be attached to the hand held tool.

Alternatively or in addition, the mount may form an integral part of the hand held tool.

Further embodiments of the fourth aspect of the present invention may comprise one or more features of the first to third aspects of the present invention.

According to the fifth aspect of the present invention there is provided a hand held tool monitoring method comprising the steps of: providing a vibration sensor of the hand held tool monitoring apparatus as part of a hand held tool; operating the vibration sensor to sense vibration of the hand held tool and provide a vibration signal in response to sensed vibration; operating a timer of the hand held tool monitoring apparatus in dependence on the vibration signal to record a duration of vibration of the hand held tool; displaying a message on a display of the hand held tool monitoring apparatus, the message being based on at least one of: a recorded duration of vibration; and information relating to a sensed vibration level.

In use, the method according to the fifth aspect of the present invention can show an operator his vibration exposure during use of a particular tool. Thus, the apparatus may be configured to clear the display and to display a further recorded duration. Such further recorded duration may, for example, be as a consequence of further use of the same hand held tool or use of a different hand held tool.

More specifically, the vibration sensor may form part of a mount.

More specifically, the mount may be configured to be attached to the hand held tool.

Alternatively or in addition, the mount may form an integral part of the hand held tool.

Alternatively or in addition, the information relating to a sensed vibration level may comprise at least one of: an accumulated vibration level (based on recorded duration or measured vibration level) from a plurality of uses by a user of at least one hand held tool; and a vibration level (based on recorded duration or measured vibration level) for a previous use of the hand held tool monitoring apparatus.

More specifically, where the information relating to a sensed vibration level comprises an accumulated vibration level, the information may be displayed when the monitoring component is attached to the mount.

Alternatively or in addition, where the information relating to a sensed vibration level comprises a vibration level for a previous use, the information may be displayed when the monitoring component is detached from the mount.

Alternatively or in addition, the message based on a recorded duration of vibration may be a remaining exposure value for a user for a current day of use.

Alternatively or in addition, the information relating to a sensed vibration level may comprise at least one of: a vibration level measured by the vibration sensor; a warning condition at which use by a user of vibrating hand held tools should be reduced; and an alarm condition at which use by user of vibrating hand held tools should be stopped.

Alternatively or in addition, a message based on a recorded duration of vibration and a message based on information relating to the sensed vibration level may be displayed alternately.

Embodiments of the fifth aspect of the present invention may comprise one or more features of the first to fourth aspect of the present invention.

According to a sixth aspect of the present invention, there is provided communications apparatus comprising first and second Radio Frequency Identification (RFID) transceivers, the first and second RFID transceivers being configured to wirelessly transmit data between the first and second RFID transceivers.

Known RFID configurations comprise an RFID transceiver and at least one RFID transponder. The RFID transceiver irradiates the RFID transponder with an RF field modulated with a transmission request, to which the RFID transponder responds by modulating the incident RF field by means of a variable load. The RFID transceiver may also be used to transmit data to the RFID transponder, the transmitted data being stored in the RFID transponder. Thus, the known RFID transceiver has a data read/write capability. According to the sixth aspect of the present invention, two known RFID transceivers are configured to transmit data from one of the RFID transceivers to the other.

More specifically, the first and second RFID transceivers may be configured for operation at least one of: 125 kHz and 13.56 MHz.

Alternatively or in addition, one of the first and the second RFID transceivers may be configured by having its emanated RF field turned off. Thus, of the two RFID transceivers only one may have its emanated field turned on, namely the RFID transceiver that is transmitting data.

More specifically, where the RFID transceivers are operable at 125 kHz, the emanated field may be turned off by writing an appropriate command to the RFID transceiver.

Alternatively, where the RFID transceivers are operable at 13.56 MHz, the emanated field may be turned off by writing a series of '1's to the RFID transceiver after a control word containing option bits is written to the RFID transceiver.

Alternatively or in addition, the first and second RFID transceivers may be configured for handshaking between them before transmission of data from one to the other.

More specifically, the communications apparatus may comprise an RFID transponder disposed nearby the first RFID transceiver and the second RFID transceiver may be configured to receive data from the RFID transponder. When the second RFID transceiver receives data from the RFID transponder, the second RFID transceiver may be configured to wait for the first RFID transceiver to transmit data.

Alternatively or in addition, the first and second RFID transceivers may be configured for duplex transmission of data between them.

Alternatively or in addition, the first RFID transceiver may form part of a first unit and the second RFID transceiver may form part of a second unit, the first and second units being movable in relation to each other.

More specifically, the second unit may form part of monitoring apparatus configured to monitor vibration of a hand held tool.

More specifically, the first unit may form part of a base component configured to receive data from the monitoring apparatus.

Alternatively or in addition, the communications apparatus may comprise a transponder, the communications apparatus being configured to write data from the first RFID transceiver to the transponder and for the second RFID transceiver being configured to read the data written to the transponder from the transponder. Thus data is conveyed from the first transceiver to the second transceiver via the transponder. According to this form, there is no need to turn off the emanated field of a transceiver.

Further embodiments of the sixth aspect of the present invention may comprise one or more features of the first to fifth aspects of the present invention.

BRIEF DESCRIPTION OF DRAWINGS

Further features and advantages of the present invention will become apparent from the following specific description, which is given by way of example only and with reference to the accompanying drawings, in which:

FIG. 1 is a view of components of a first embodiment of the present invention;

SPECIFIC DESCRIPTION

Figure 2A:
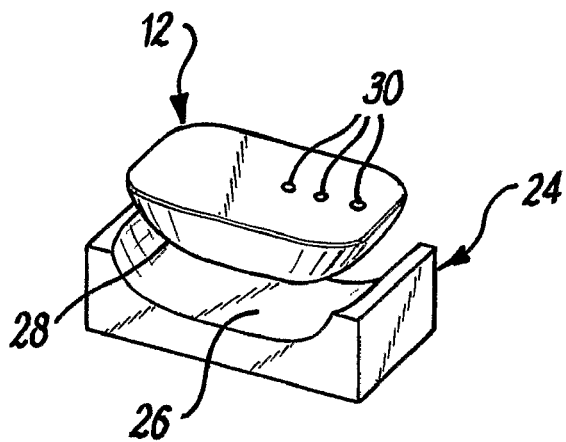
FIGS. 2A to 2C are detailed view of certain components shown in FIG. 1.

A hand held apparatus 10 according to a first embodiment of the present invention is shown in FIG. 1. The hand held apparatus 10 comprises a monitoring component 12, which has a vibration sensor and a timer, a base component 14, a user identification (ID) card 16 (which constitutes a user identification component), a Multimedia Card (MMC) 18 and a Personal Computer 20. In this instance the hand held apparatus 10 is being used with a pneumatic drill 22.

The user ID card 16 is used to identify the user, e.g. an employee and store information relating to the user. The user ID card is of a Hi Coercivity Magstripe type, which means that it will be more difficult for a user to remove the data by putting the card close to a magnetic field. The user ID card can be printed and encoded by a combination printer according to a predetermined format, e.g. by an employer. A card can store 1288 bits of information comprising user information to a total of 56 bits with the remainder of the data space available for training and/or Health and Safety information. The user information comprises: an ID card identification number (of 64 bits); a 10 digit user identification number (of 64 bits); a sensitivity level for the user (of 8 bits); an exposure action value (of 16 bits); an exposure limit value (of 16 bits); and an error reporting code (of 16 bits).

In addition to user ID cards, an authorisation card may be used. Use of an authorisation card provides for additional functionality of the base component 14. More specifically, the authorisation card can be used to:

i) Set the real time clock;
ii) Manually release a monitoring component from the base component; and
iii) Enable and disable the base component for all users.

The data structure of the authorisation card is as follows:

| Data | Size and Type | Description |
|---|---|---|
| Person ID | 64-bit Integer | A unique identifier for the person who is using the authorisation card |
| Action Code | 8-bit Integer | A series of flags indicating what was done in the authorisation mode. The possible actions are:<br>1. Manual entry of a user<br>2. Change date<br>3. Change time<br>4. Change data copy timer<br>5. Change of authorisation requirement |
| Time | 16-bit Integer | Value giving the time of day the authorisation card was used |
| Date | 16-bit Integer | Value giving the date that the authorisation card was used |

Figure 2B:
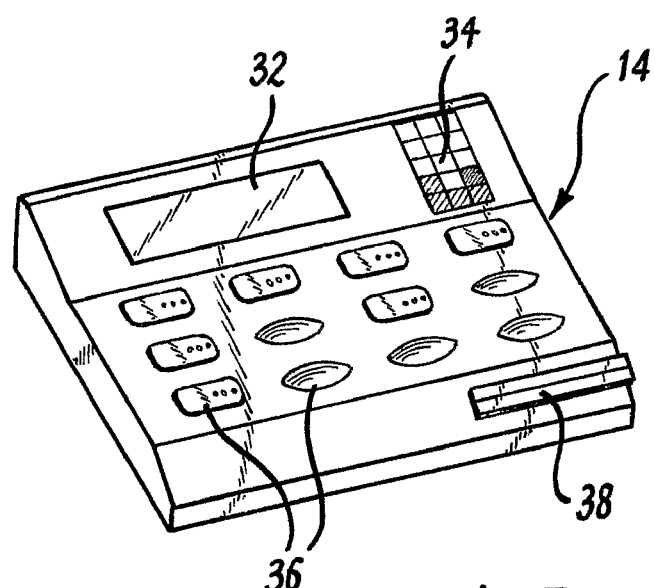
Figure 2C:
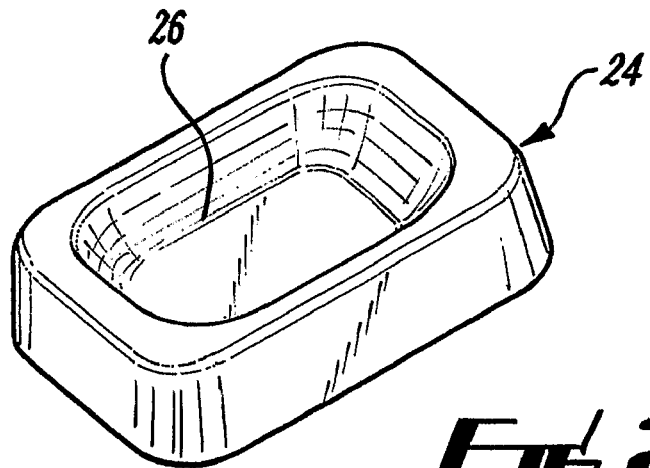

FIGS. 2A to 2C provide detailed views of the monitoring component 12 and the base component 14 shown in FIG. 1 along with a mount 24 for attaching the monitoring component 12 to the pneumatic drill 22 of FIG. 1. In use, the mount 24 is attached to the pneumatic drill 22, although the mount is not evident from FIG. 1.

In an alternative (un-illustrated) form of the invention, the mount is formed integrally with the pneumatic drill with the casing of the mount forming an integral part of the casing of the pneumatic drill.

FIG. 2A shows the monitoring component 12 and the mount 24. The monitoring component 12 and the mount 24 have respective cooperating magnetic components (not shown) that in use provide for releasable attachment of the monitoring component 12 to the mount 24. Also, the mount 24 has a generally concave surface profile 26, which is shaped to receive a generally convex surface profile 28 of the monitoring component 12. The monitoring component 12 has three visual indicators (which constitutes an indicator configured to indicate a vibration value in dependence on the vibration signal), which respectively display green, amber and red. Operation of the green indicator indicates that a vibration level is below a warning level value, operation of the amber indicator indicates that a vibration level is above the warning level value and operation of the red indicator indicates that a vibration level is above an exposure limit value.

In an un-illustrated embodiment, the monitoring component 12 has a three digit display in addition to the three visual indicators. The three digit display is of conventional design and operation. In use, the three digit display displays a remaining exposure value for the user for the current day of use on an alternating basis with either an accumulated exposure value for the user (for uses with two or more tools on the current day of use) or the last exposure value for the most recently used tool. The accumulated exposure value for the user is displayed when the monitoring apparatus is attached to a tool. The last exposure value is displayed when the monitoring apparatus is detached from a tool. The appropriate exposure values alternate with each other at five second intervals. The exposure values are displayed on the three digit display in accordance with a points system devised by the United Kingdom Health and Safety Executive. Thus, the remaining exposure value is displayed in terms of points left for the current day out of a maximum of 400, which represents the safe daily limit for the user. The following table provides a summary of the messages displayed on the three-digit display:

| State | Description | Cancel Condition |
|---|---|---|
| Show Nothing | Nothing is shown on the screen | — |
| Last Tool Points | Number of points used whilst on the last tool | — |
| Total Points Used | Total number of points used that day | — |
| Tool Total Points | Total points used on this tool covering all uses during the day | — |
| "BAT" | Indicates that the battery is low screen, literally shows, 'BAT', although, the T will be displayed as a 7 because a seven segment can't display a full, 'T' | — |
| "HI" | Indicates the overdose level for this tool has been exceeded, literally shows, 'HI' | — |
| "CAL" | Indicates that the device is in a calibration mode, literally shows, 'CAL'. This is for use during calibration activities | — |
| "E01" | HAV unit has been removed from base station without swipe card identification and has been attached to a valid tool | Remove HAV unit from tool |
| "E02" | HAV unit has been placed on a base station which has not responded correctly | Remove HAV unit from base station |
| "E03" | HAV unit has been placed on an unknown device which has triggered the connection detect | Remove HAV unit from unknown device |

The monitoring component 12 (which is termed a 'HAV unit' in particular in the tables) has a permanently installed internal rechargeable battery (not shown) of a kind that does not suffer from battery memory problems. Charging of the rechargeable battery is by way of either a wired coupling or an inductive coupling between the monitoring component 12 and the base component 24, which is shown in FIG. 2B. The wired and inductive couplings between the monitoring component 12 and the base component 24 (which is termed 'base station' in particular in the tables) are of conventional design and operation. The rechargeable battery has the capacity to power the monitoring component 12 in full use for a minimum of 16 hrs between recharges. This is considered sufficient for use over an employee user's full working shift plus extra power for overtime. It is expected that most period of use of the monitoring component 12 is around 9 hours. Thus, most recharges will be from a 40% charge level. Thus, the battery has a fast recharge over the commonly used first 60% of charge at a ratio of 1:4 for recharge: discharge times. Also, the battery has a slower recharge speed for charging to the 40% level at a ratio of 1:2 for recharge: discharge times.

FIG. 2B shows the base component 14, which comprises a display 32 consisting of an array of dot matrix characters. The dimensions of the array are 25×4 (width by height) with each dot matrix character being at least 8×5 pixels in at least a 5×3 mm area. The base component 14 also has a keypad 34 having the standard twelve button telephone keys with the hash and star keys replaced with left and right arrows. A further key (not shown) is provided to function as an enter key. Appropriate graphics are displayed on the keys. The base component 14 has an array of docking bays 36, each of which is configured to receive a monitoring component 12. In addition, the base component 14 has an RFID read/write device 38 for communicating with a monitoring component 12.

In addition, the base component 14 has a magnetic strip card reader for reading the user ID card 16, which is shown in FIG. 1. The base station is capable of receiving power from a 12V DC power supply (not shown). One configuration involves use of external power supply units which connect to generator supplies or to the mains. Another configuration involves use of automobile DC voltage supplies.

FIG. 2C shows an alternative form of the mount 24 according to which the concave surface profile 26 is shaped to completely encircle the convex surface profile 28 of the monitoring component 12.

Both the monitoring component 12 and mount 24 have a plastics enclosure that is capable of being repeatedly covered in concrete splashes and cleaned whilst maintaining reliable operation. The enclosure of the monitoring component 12 and mount 24 are rated to IP65. The enclosure of the base component 14 rated to IP54.

Figure 3:
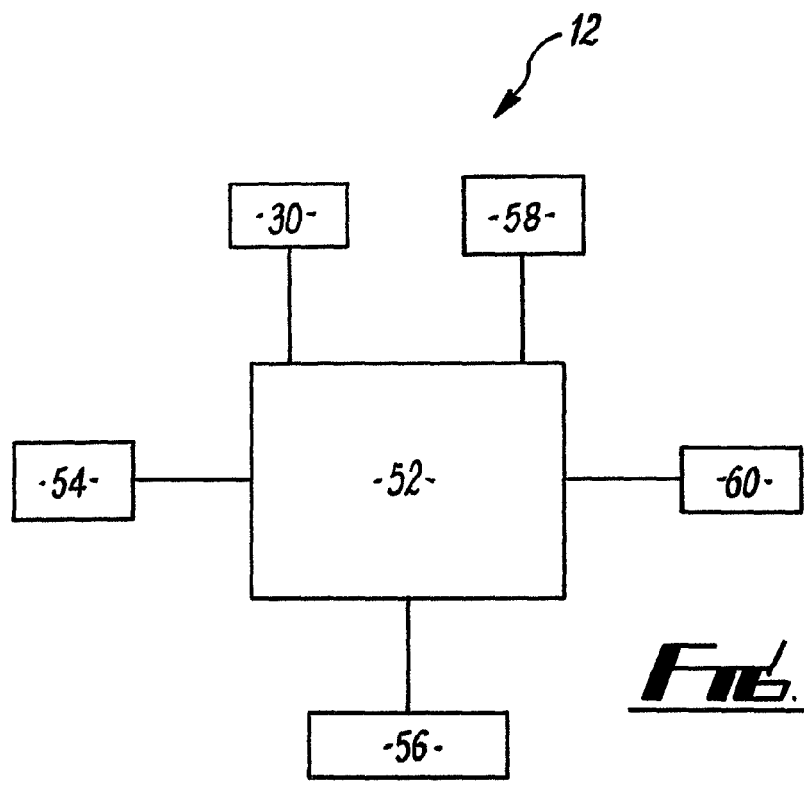
FIG. 3 is a block diagram schematic for a monitoring component according to the first embodiment.

The monitoring component 12 is shown in FIG. 3 in block diagram form. The monitoring component 12 has three coloured indicators 30, a microprocessor 52, memory 54, two tri-axial accelerometers 56 (which constitute a vibration sensor), a reed switch 58 and an RFID interface 60. The microprocessor 52 controls the operation of the monitoring component 12 and amongst other things performs a timer function. The microprocessor 52 is an Analog Devices 400 MHz DSP enabled Blackfin (BF531SBBCZ400). Firmware code is stored in the monitoring component in the memory 54, namely ST Microelectronics 1 Mb low voltage serial flash memory with an SPI interface. The maximum 'on' state that the accelerometers 56 reliably detect is not above the accelerometers' maximum acceleration rating. Signals from the accelerometers 56 are converted from an analogue to a digital form by a National Semiconductor ADC124SO21 analogue-to-digital converter. The accelerometers have typical dimensions of about 8×8×3 mm. The specifications for the first kind of accelerometer are shown in the following table:

| Parameter | Min | Max |
|---|---|---|
| Freq range (Hz) | 1 | 1500 |
| Peak acceleration range (m/s$^2$) | — | 6 |
| Dimensions (mm) | — | 5.5 * 5.5 * 1.5 |
| Abs Noise (m/s$^2$) | — | 0.5 |

The first kind of accelerometer is an LIS3L06AL from ST Microelectronics, which is tri-axial.

The second kind of accelerometer has the following specifications:

| Parameter | Min | Max |
|---|---|---|
| Freq range (Hz) | 1 | 1500 |
| Peak acceleration range (m/s$^2$) | — | 60 |
| Dimensions (mm) | — | 5.5 * 5.5 * 1.5 |
| Abs Noise (m/s$^2$) | — | 0.1 |

An MMA1200 from Freescale is used for the z-axis and an ADXL193 from Analog Devices is used for each of the other two axes (i.e. x and y) of the second kind of accelerometer.

The microprocessor is operative to select vibration signals produced by one of the above two types of accelerometer on the basis of the maximum acceleration detectable by each accelerometer. Thus, for example, if the vibrations produced by a tool being monitored have acceleration values below a low maximum value of acceleration vibrations from the accelerometer having the lower maximum detectable acceleration will be selected. The reed switch 58 is operative to power up the monitoring component 12 when it is received in the mount 24. In a form of the invention, a push button switch may be used instead of the reed switch. In this form of the invention, the push button switch is located such when the monitoring component is attached to the mount the push button switch is actuated.

When the monitoring component 12 is received in the mount the RFID interface 60 is operative to actuate a passive RFID tag contained in the mount (not shown) thereby triggering the transmittal of information relevant to the hand held tool, including information on vibration, to the monitoring component. The three coloured indicators 30 are operated as shown in the following table:

| Dose level (greater than) | Alarm | Employee action (person at normal risk) |
|---|---|---|
| Zero | GREEN light - solid on | |
| Exposure Action Value [EAV A(8)] | ORANGE light - slow flashes | Reduce use of vibrating tools |
| Exposure Limit Value [ELV A(8)] | RED light - fast flashes | Stop use of vibrating tools for the day |

To differentiate visual warnings for those who are colour blind the indicators operate in accordance with the above table. Alarm levels are adjusted for individuals having increased 'sensitivity' due to signs of HAV damage.

| Light Sequence | Event | Action |
|---|---|---|
| No Lights (whilst connected to a tool) | Monitoring component is broken or out of batteries | If recharging is not effective send monitoring component for repair |
| Solid Green Light (whilst connected to a tool) | Monitoring component functioning correctly. Under EAV | None |
| Solid Green Light (whilst connected to base component) | Monitoring component recharged and ready for use | None |
| Slow Flashing Amber Light | Action level has been reached. | Reduce usage of high vibration equipment |
| Fast Flashing Red Light | Limit level has been reached | Stop use of all vibrating equipment |
| Flashing Green Light | Monitoring component is running low | Return unit for a recharge |
| All lights flashing simultaneously | Tool needs servicing | Disconnect monitoring component and retest tool then inform foreman Select a different tool |
| Strobe across lights for 30 secs (whilst connected to base component) | Monitoring component is recharging in the base component | Do not remove from base component |
| All lights illuminated (whilst connected to base station) | Identifies the monitoring component that should be removed from the base station | Remove monitoring component for use |

Figure 4:
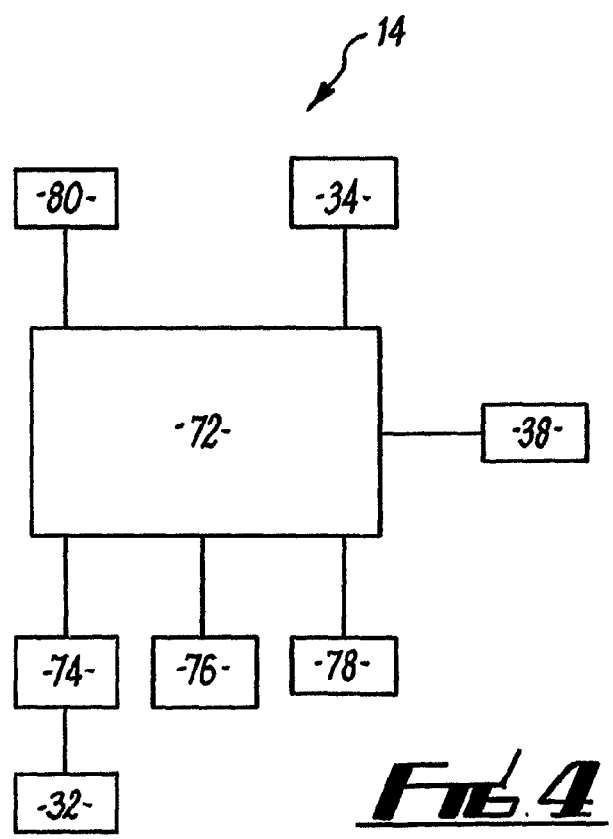
FIG. 4 is a block diagram schematic for a base component of the first embodiment.

The base component 14 is shown in FIG. 4 in block diagram form. The base component 14 comprises a microprocessor 72, a display driver 74 and display 32, an MMC card interface 76, a clock 78, an RFID interface 38, a keypad 34 and LEDs 80. The microprocessor 72 in the base component 14 is an 8-bit 16 MHz microprocessor, namely an Atmel AT Mega 325-16. Memory is integral to the microprocessor 72.

Firmware for both the monitoring component 12 and the base component 14 is stored in local memory having been developed in a computer-based environment before being compiled and downloaded to local memory. The steps of firmware development, compilation and download into local memory are in accordance with practice that is well known to the skilled person.

The data storage format for the first embodiment will now be described.

The time and date format used in the monitoring component 12 and the base station 14 is as follows. Time is stored as a 16-bit integer. The value of this integer is multiplied by the tick speed of the system of 1.32 seconds to obtain the number of seconds that have passed since the start of the day. The date is also stored in a 16-bit integer format as per the table below:

| Day | Month | Year |
|---|---|---|
| 5-Bit Integer | 4-Bit Integer | 7-Bit Integer |

Within the monitoring component 12 the following table shows data permanently held within the component:

| Data | Size and Type | Description |
|---|---|---|
| Unit ID | 64-bit Integer | A unique identifier given to each monitoring component 12 when it is |

-continued

| Data | Size and Type | Description |
|---|---|---|
| Version | 32-bit Integer | produced A version number for the device firmware, this is used to check that the base component 14 and monitoring component 12 are compatible |

The Unit ID should be uploaded to the base component 14 just before the monitoring component 12 is removed from the base component 14. This allows the base component to track monitoring components. The following table shows data transmitted to the monitoring component 12 just before it is removed from the base component 14:

| Data | Size and Type | Description |
|---|---|---|
| Person ID | 64-bit Integer | The unique identifier from the user ID card 16 |
| Sensitivity | 8-bit Integer | Values 0 and 1 will cause the normal EAV and ELV to be used. Higher values will cause the EAV to be set as ½ the EAV and the ELV to be replaced with the EAV |
| Init. Base ID | 64-bit Integer | A 64-bit unique identifier for the base component the monitoring component was removed from |
| Init. Time | 16-bit Integer | Value giving the time of day the monitoring component was removed from the base component, read from the base component clock |
| Init. Date | 16-bit Integer | Value giving the date the monitoring component was removed from the base component, read from the base component clock |
| EAV value | | |
| ELV value | | |

The following data is collected during use of the monitoring component and relates to broken tool, e.g. the pneumatic drill 22 of FIG. 1, and vibration data:

| Data | Size and Type | Description |
|---|---|---|
| Action Time | 32-bit Integer | Time stamp written when the user reaches his action value |
| Limit Time | 32-bit Integer | Time stamp written when the user reaches his limit value |
| Exposure | 16-bit Integer | Current A(8) exposure value of user |
| Broken Tools | 10x 48-bit Integers | An array of up to 10 Tool IDs, as read from the tools. Tool IDs will be written into this list if the tool is determined to need servicing |
| Vibration Record | 1000 x 152-bit Structures | An array of tool usage records. Defined in the table immediately below |

Each entry in the vibration record consists of the following fields:

| Data | Size and Type | Description |
|---|---|---|
| Tool ID | 64-bit Integer | Tool ID of the tool that the monitoring component was connected to |
| Tag ID | 64-bit Integer | Identifier for the RFID tag in the tools cradle |
| Connect | 32-bit Integer | Time stamp of when the tool was connected to the monitoring component |
| Disconnect | 32-bit Integer | Time stamp of when the tool was disconnected from the monitoring component |
| Trigger Time | 16-bit Integer | Total amount of trigger time whilst connected to the tool |
| Tool Dose | 32-bit Float | The dose rating taken off the mount |
| Vibration Indicator | 32-bit Float | An indicator of how close the tool is to its rated level |
| Flags | 8-bit integer | Status flags. One flag indicates whether or not a vibration overdose occurred during use of the tool |

The structure of data stored in the mount's RFID tag is set out in following table.

| Data | Size and Type | Description |
|---|---|---|
| Tag ID | 64-bit Integer | A unique identifier for this tag. |
| Tool ID | 64-bit Integer | A unique identifier for the tool. |
| $C_{xn1}$ | 16-bit Integer | X axis isolation filter, coefficient. |
| $C_{xn2}$ | 16-bit Integer | X axis isolation filter, coefficient. |
| $C_{xn3}$ | 16-bit Integer | X axis isolation filter, coefficient. |
| $C_{xd2}$ | 16-bit Integer | X axis isolation filter, coefficient. |
| $C_{xd3}$ | 16-bit Integer | X axis isolation filter, coefficient. |
| $G_x$ | 16-bit Integer | X axis isolation filter, gain. |
| $C_{yn1}$ | 16-bit Integer | Y axis isolation filter, coefficient. |
| $C_{yn2}$ | 16-bit Integer | Y axis isolation filter, coefficient. |
| $C_{yn3}$ | 16-bit Integer | Y axis isolation filter, coefficient. |
| $C_{yd2}$ | 16-bit Integer | Y axis isolation filter, coefficient. |
| $C_{yd3}$ | 16-bit Integer | Y axis isolation filter, coefficient. |
| $G_y$ | 16-bit Integer | Y axis isolation filter, gain. |
| $C_{zn1}$ | 16-bit Integer | Z axis isolation filter, coefficient. |
| $C_{zn2}$ | 16-bit Integer | Z axis isolation filter, coefficient. |
| $C_{zn3}$ | 16-bit Integer | Z axis isolation filter, coefficient. |
| $C_{zd2}$ | 16-bit Integer | Z axis isolation filter, coefficient. |
| $C_{zd3}$ | 16-bit Integer | Z axis isolation filter, coefficient. |
| $G_z$ | 16-bit Integer | Z axis isolation filter, gain. |
| Primary-axis | 8-bit Integer | Indicates which of the 3 axes is the primary vibration axis for this tool and hence, should be used for on/off detection. |
| On-limit | 16-bit | Gives the level that should be |

-continued

| Data | Size and Type | Description |
|---|---|---|
| | Integer | used as a threshold to determine if the tool is in use. |
| Off-limit | 16-bit Integer | Gives the level that should be used as a threshold to determine if the tool is no longer in use. |
| On-duration | 16-bit Integer | The length of time use to determine when the tool is no longer in use. |
| Over-dose | 16-bit Integer | Gives an RMS level that should be used as a threshold to determine when the tool is exceeding acceptable vibration levels. |
| Dose-level | 16-bit Integer | Gives the vibration level, in scaled points, that should be used for vibration dose calculations on this tool. |

The above data allows several aspects of tool usage to be investigated. The tool ID allows for identification of the tool that has been used. Connect and disconnect time show the time of day the tool was used and how long the user spent using this tool. Trigger time and tool dose can be used together to calculate a user's vibration exposure whilst using the tool. Furthermore, connect and disconnect time can be combined with trigger time to show the ratio of time spent on the tool to the time the tool was actually being used. Also, the vibration indicator can be used to assess the vibrations produced by the tool in relation to its rated vibration level (see following section).

The data detailed in the four tables above is written back to the base component 14 when the monitoring component 12 device is returned at the end of the day.

Permanent data held on the base component 14 is listed in the following table. With the exception of device identification data, this data consists of initial base station data and final base station data.

| Data | Size and Type | Description |
|---|---|---|
| Device ID | 8-bit Integer | An identifier indicating that this is a base component. Two base component identifiers exist one indicating a simple recharge base component and the other indicating a full base component. This is the only information held on the passive RFID tag contained within the base component |
| Base ID | 64-bit Integer | A unique identifier given to each base component when it is produced |
| Version | 32-bit Integer | Indicates the version number of the base component software |
| Time | n/a | The current time, this is accessed on the external clock module. Although, this will be converted into a 16-bit time stamp, before being given to a monitoring component, as discussed above |
| Date | n/a | The current date, this is accessed on the external clock module. Although, this will be converted into a 16-bit format, before being given to a monitoring component HAV, as discussed above |

When a monitoring component 12 is about to be removed from the base component 14 the information in the table above will be downloaded to that unit, as well as the information read from the user ID card 16. The time and date are converted into their 16-bit representations before being transferred on.

A list of monitoring components that have been removed from the base component is maintained within the base component. This is shown in the following table:

| Data | Size and Type | Description |
|---|---|---|
| HAV ID | 64-bit Integer | A unique identifier for the monitoring component that was removed, this must be read from the monitoring component just before it is removed |
| Person ID | 64-bit Integer | A unique identifier for the person that removed the monitoring component, taken from the user ID card |
| Time | 16-bit Integer | A time stamp indicating the time the monitoring component was removed |
| Date | 16-bit Integer | A time stamp indicating the date on which the monitoring component was removed |

Upon return of the monitoring component 12 to the base component 14 the data is transmitted from the monitoring component 12 to the base component 14 and then stored on the MMC card 18 of FIG. 1. All communications between the base component and the monitoring component are error checked using a Cyclic Redundancy Code (CRC) or similar Forward Error Correction (FEC) code. Data is resent should it not arrive intact. The structure of the data downloaded to the base component is given in the following table:

| Data | Size and Type | Description |
|---|---|---|
| Base ID | 64-bit Integer | A unique identifier for this base station |
| Return Time | 16-bit Integer | Value giving the time of day the unit was returned to the base station |
| Return Date | 16-bit Integer | Value giving the date that the unit was returned to the base station |

The following table lists error messages the base component can present. The table also describes the situation in which these messages appear. #bay refers to the number of the docking bay 36 of the base component that the monitoring component 12 is located in.

| Code | Text | Cancel Condition | Description |
|---|---|---|---|
| M1 | "Communications to HAV unit failed: #bay" | 30 second timeout | The base station was unable to download the information from the HAV unit in the given bay |
| M2 | "HAV Unit not collected" | 5 second timeout | Someone asked for a HAV unit but never collected it from the base station. Accompanied by a red LED. |

-continued

| Code | Text | Cancel Condition | Description |
|---|---|---|---|
| M3 | "Copying data to memory card . . ." | Memory card full | Someone has inserted a memory card and data is being copied to it |
| M4 | "Copying complete" | 5 second timeout | All data awaiting transfer has been successfully uploaded, accompanied by green LED |
| M5 | "Change memory card" | Memory card is replaced or alarm is turned off | The memory card should be replaced with a fresh one |
| M6 | "Swipe card invalid" | 5 second timeout | A card was swiped that was not recognised |
| E1 | "All HAV units in use or charging" | 5 second timeout | A HAV unit can't be released because they are all charging or in use. Accompanied by a red LED |
| E2 | "Unknown release error" | 5 second timeout | A HAV unit can't be released for unknown reasons, units where available, however, the release process failed. Accompanied by a red LED |
| E3 | "Memory card corrupted" | Memory card is removed | An invalid memory card has been inserted or the card has broken. Accompanied by a red LED |
| E4 | "Memory card transfer failed." | 5 second timeout | A memory card has been removed or broken during data transfer. Accompanied by a red LED |
| E5 | "Memory card full - please insert another card" | Memory card removed | A memory card is already full and there is further data to transfer. Accompanied by a red LED |
| E6 | "Internal memory card corrupted" | Memory card is replaced | An invalid memory card has been inserted or the card has broken. Accompanied by a red LED |
| E7 | "Unknown fatal error" | Can't be cleared | An error has occurred which requires the HAV unit to be returned to the manufacturers. Accompanied by a red LED |

The base component 14 memory storage subsystem consists of two MMC cards 18. The first of these cards is easily removable and intended to allow data from the base component to be transported to a Personal Computer 20, which functions as a central server. The second card is internal with some access to the second card being provided for upgrade purposes. The internal card is much larger in storage capacity than the external card and acts as a data back-up facility to prevent permanent loss of data in the event of damage or loss of external card. The internal card contains two types of file.

The first type of file will have the extension, ".dat", and contains vibration records. This file contains a header and then a continuous list of vibration records. The format of the header is given in the following table:

| Name | Size | Description |
|---|---|---|
| Base Station ID | 32-bit Integer | Unique identifier for the base component that recorded this file. |
| Base Station Version | 32-bit Integer | The version number of the base component that recorded this file |

The format of a record is given in the following table:

| Name | Size | Description |
|---|---|---|
| Capture String | 3x 8-bit Characters | A string consisting of the characters, "REC", stored in standard ASCII and used to identify the start of a record. |
| Initial Base Station Version | 32-bit Integer | The version number of the initial base component. |
| Size | 32-bit Integer | The size of the initial base component data. |
| Data | N/A | The actual data from the initial base component. |
| HAV Version | 32-bit Integer | The version number of the monitoring component that took the recording. |
| Size | 32-bit Integer | The size of the monitoring component data. |
| Data | N/A | The actual data from the monitoring component. |
| Final Base Station Version | 32-bit Integer | The version number of the final base component. |
| Size | 32-bit Integer | The version number of the final base component. |
| Data | N/A | The actual data from the final base component. |
| End String | 3x 8-bit Characters | A string consisting of the characters, "END", stored in standard ASCII and used to identify the end of a record. |

A new .dat file is started every time the external card is replaced. This means that the files correspond to data recorded between cards being taken to the central server 20 making data recovery easier. The .dat files are given an 8-digit number as an identifier. Thus, the first file reads "00000001.dat". These file names should increment each time a new file is created.

The second type of file has the extension ".rem". This type of file contains a list of monitoring components that have been removed from the base component during the day. This type of file also contains a header and a continuous list of records. Files are numbered in the same manner as the .dat files and new files are started at the same time. The header is identical to that of the dat file. The format of the records is shown in the table below:

| Name | Size | Description |
|---|---|---|
| Capture String | 3x 8-bit Characters | A string consisting of the characters, "REC", stored in standard ASCII and used to identify the start of a record. |
| Size | 32-bit Integer | The size of the record. |
| Data | N/A | The actual data from the base component about monitoring component removal. |
| End String | 3x 8-bit Characters | A string consisting of the characters, "END", stored in standard ASCII and used to identify the end of a record. |

Figure 5:
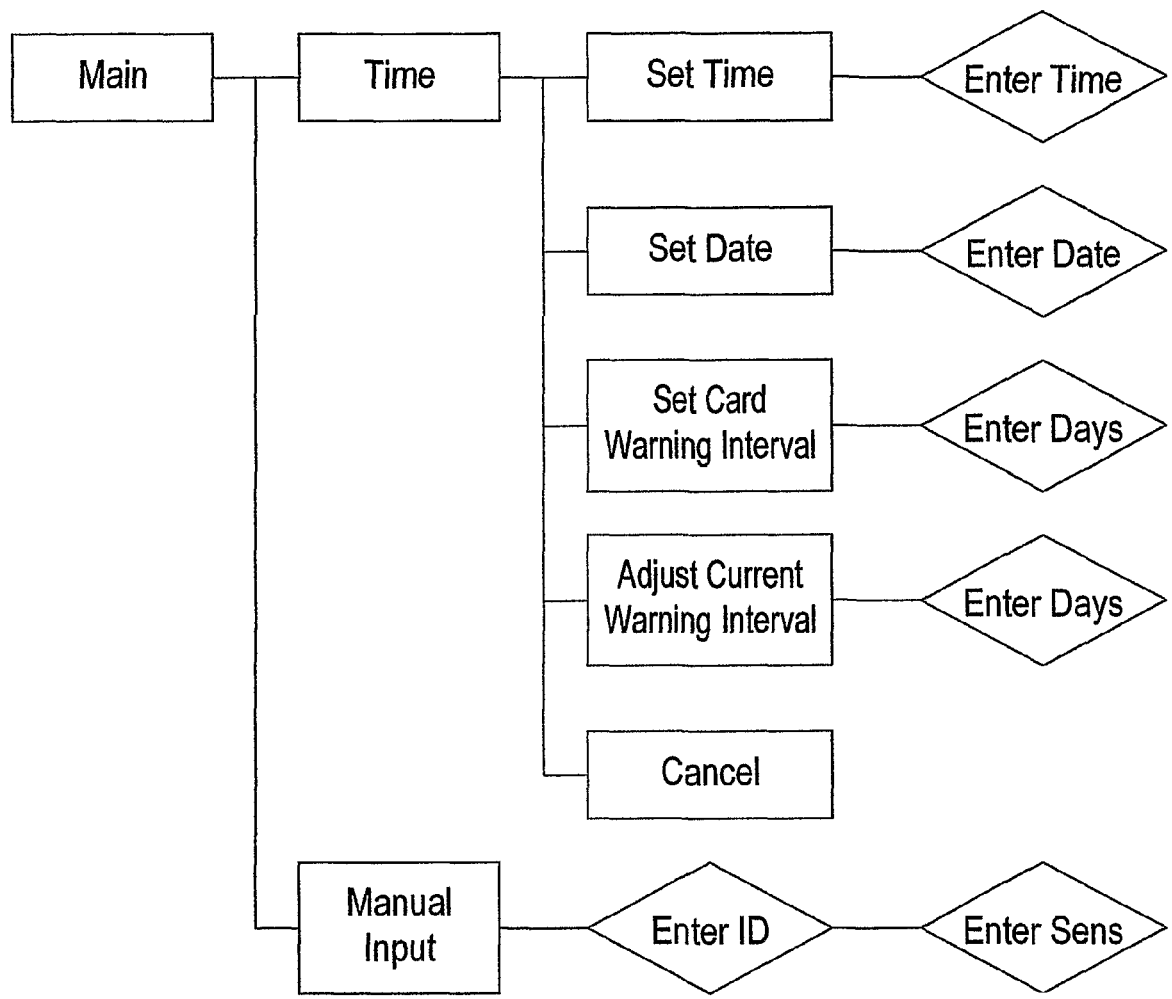
FIG. 5 is a flow chart illustrating a sequence of steps of operation of the base component of the first embodiment.

The arrangement of menus that are displayed on the screen of the base component is shown in FIG. 5. The square boxes represent menu options and the diamonds represent where user input is required. The "Main" state as shown at the root of FIG. 5 is the default state of the display procedure. At any point should the display procedure be left idle in one of the sub-states, for more than 30 seconds, it will return to the main state. This state displays the time and flashes through the list of current warnings should any exist, displaying each warning for 5 seconds. For each sub-state menu the options can be iterated through using the left and right keys on the base component and then selected using the enter key. Each of the data entry screens consist of a number of fields into which numbers can be typed from the keypad. These fields can be moved between using the left and right keys. Whichever field has the input focus will accept keypad data. After iterating past the last data entry field two further menu options are provided, namely Save and Cancel. The following table describes each of the diamond boxes in more detail:

| Name | Description | OK Actions |
|---|---|---|
| Enter Time | Used for setting the time; contains 3 colon separated values (hours (0-24), minutes (0-60), seconds (0-60)). | Updates time on the base component. |
| Enter Date | Used for setting the date, contains 3 slash separated values (day(1-31), month(1-12), year (2000-2128)) | Updates the date on the base component. |
| Enter Days | Used for setting certain timers, contains only 1 value (days). Displayed as the number followed by a space and the string "days". | Updates the relevant timer period. |
| Enter ID | Used for entering a Person ID in the advent of an employee forgetting one. Contains only one value (10 digit). Displays the string "PID:", followed by a space and then the digits appear as the user types them in. | |
| Enter Sens | Used for entering a person's sensitivity rating. Contains only one value (0-255). Used in place of swipe card for releasing a monitoring component. Displays the string "Sens:", followed by a space and then the digits appear as entered by the user. | Initiates a monitoring component release much as a card swipe would. |

The vibration levels are calculated within the monitoring component 12 in accordance with the following procedure. It should be noted that tests with sample power tools have shown a very good correlation between vibration signatures seen in the position of a mount on the tool casing and those seen in the tool handle position. Vibration signatures at the tool handle position are necessary to meet United Kingdom HSE testing procedures for tool assessment. Recording of RMS values of vibration seen at the mount are another useful part of tool management and give a good indication of actual vibration levels being experienced by users. The procedure used to calculate the vibration levels at the mount follow the procedure outlined in legislation for HAV measurements on the handle. The vibration signals are filtered by an isolation filter to emulate the effect of an isolated handle on a power tool. It will automatically change the recorded vibration so that it better represents what would be experienced by the hands and arms of a user of the isolated tool. The isolation of the tool is characterised and represented numerically within the isolation filter. The isolation filter consists of a bank of three second order filters; one filter for each axis of vibration. The equation below shows the structure of the isolation filter. The eighteen coefficients in the equation, six for each filter, are stored in the mount 24 and are determined for each tool type having an isolated handle.

$$O = G \frac{c_{n_1} Iz^0 + c_{n_2} Iz^{-1} + c_{n_3} Iz^{-2} - c_{d_2} Oz^{-1} - c_{d_3} Oz^{-2}}{c_{d_1}}$$

Subsequent procedure involves three steps:

1. The monitoring component weighting curve. The 3-axis vibration signal from one of the accelerometers is passed through a special filter that weights the different frequencies in relation to harmfulness. This filter is composed of a band-limiting filter cascaded with a frequency-weighting filter. Both the filters are defined in the standard Laplace representation. The band-limiting filter is defined as:

$$H_b(s) = \frac{s^2 4\pi f_2^2}{\left(s^2 + \frac{2\pi f_1 s}{Q_1} + 4\pi^2 f_1^2\right)\left(s^2 + \frac{2\pi f_2 s}{Q_1} + 4\pi^2 f_2^2\right)}$$

$$f_1 = 6.31, \ f_2 = 1258.9, \ Q_1 = 0.71$$

The frequency-weighting filter is defined as:

$$H_w(s) = \frac{(s + 2\pi f_3) 2\pi K f_4^2}{\left(s^2 + \frac{2\pi f_4 s}{Q_2} + 4\pi^2 f_4^2\right) f_3}$$

$$f_3 = 15.915, \ f_4 = 15.915, \ Q_2 = 0.64, \ K = 1$$

These two filters are cascaded as follows:

$$H(s) = H_b(s) \Box H_w(s)$$

2. An RMS (Root Mean Square) of each axis. This produces a single figure that describes the amplitude of the vibration signal. An RMS is defined as (shown for the x-axis with the y and z axes defined in an identical fashion):

$$a_{hwx} = \sqrt{\frac{1}{N}\sum_{k=1}^{N} x_k}$$

3. Axis Averaging. The three axes of measurement are combined into a single figure, defined as:

$$a_{hv} = \sqrt{a_{hwx}^2 + a_{hwy}^2 + a_{hxz}^2}$$

The above procedure derives a single measure of tool vibration. Over time a picture can be built up of the distribution of vibration values simply by graphing the density of the values returned by the system whilst in the field. Comparison of these values to dose levels on the tools as measured in line with United Kingdom HSE testing procedures for tool assessment is tool specific and as such requires testing to determine the relationship for each tool.

The physical characteristics of the monitoring component 12, the base component 14, the user ID card 16 and the mount 24 are given in the following tables.

| Monitoring component | | |
|---|---|---|
| Size | | |
| Max | 90 × 50 × 25 | mm |
| Preferred | 50 × 30 × 20 | mm |
| Min | 45 × 25 × 13 | mm |
| Weight | | |
| Max | 175 | grams |
| Min | 30 | |
| Base component | | |
| Size | | |
| Max | 810 × 450 × 225 | mm |
| Preferred | 450 × 270 × 180 | mm |
| Min | 405 × 225 × 117 | mm |
| Weight | | |
| Max | 5 | Kg |
| Bay Spacing (HAV units mounted on ends) | | |
| Horizontal Max | 60 | mm |
| Horizontal Preferred | 80 | mm |
| Horizontal Min | 100 | mm |
| Vertical Max | 60 | mm |
| Vertical Preferred | 80 | mm |
| Vertical Min | 100 | mm |
| User ID Card | | |
| Size | | |
| Max | 90 × 60 × 1 | mm |
| Preferred | 85 × 55 × 0.5 | mm |
| Min | 80 × 50 × 0.5 | mm |
| Mount | | |
| Size | | |
| Max | 95 × 55 × 10 | mm |
| Preferred | 55 × 35 × 5 (monitoring component area + 10%) | mm |
| Min | 45 × 25 × 2 | mm |
| Weight | | |
| Max | 50 | grams |

Operation of the first embodiment of the present invention will now be described with reference to FIG. 6.

The present invention performs three major complementary functions: health and safety management in accordance with UK HAV legislation; user management; and tool management.

Figure 6:
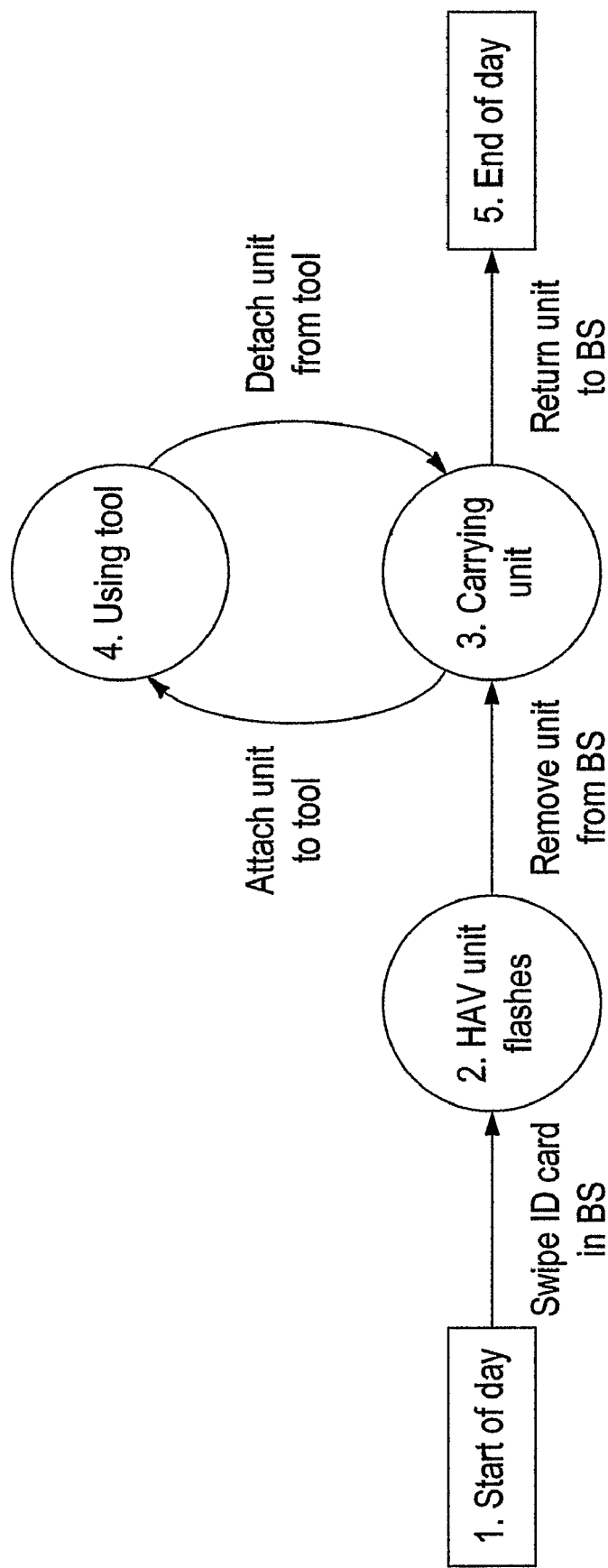
FIG. 6 is diagram illustrating typical daily use of the first embodiment.

Referring to FIG. 6, a user reports for work at a site. The user enters the site hut (or site van) with his personal user ID card 16. He swipes his user ID card 16 at the base component 14 to uniquely identify himself to the system. If the user has forgotten his card he is able to identify himself to the system by keying in his payroll number using the keypad 34 on the base component. The base component saves the employee ID and the current time to one of the monitoring components 12 docked there, which is then released for use. The monitoring component has been fully charged while resting at the base component and is synchronised with the base component clock. When the monitoring component has been removed, the base component is then free to accept the next user's user ID card 16 and release a further monitoring component. The user carries the rugged, water resistant monitoring component to the first tool he wants to use, e.g. the pneumatic drill 22 of FIG. 1, and clips it onto the tool body where it is held firmly within a mount 24.

The reed switch 58 turns the monitoring component 12 on. The monitoring component is triggered to use its in-built RFID (Radio Frequency Identification) read/write interface 60 device to read information from the RFID tag mounted in the mount 24. More specifically, the monitoring component 12 reads the tool ID and the vibration dosage rate for the tool. In addition, a value representing the 'trigger on' vibration level is read (which constitutes the vibration threshold value).

In an un-illustrated embodiment, the monitoring apparatus has a transponder, with the monitoring apparatus being configured to write data from a first RFID transceiver (such as that in the monitoring component) to the transponder and for the second RFID transceiver (such as that in the base station) being configured to read the written data from the transponder. Thus data is conveyed from the first transceiver to the second transceiver via the transponder. According to this embodiment, there is no need to turn off the emanated field of the transceiver receiving the data as it operates in a known manner.

As the tool is used the tri-axial accelerometers of the monitoring component produce a vibration signals for each of three axes. The microprocessor 52 is operative to select one or a combination of the three vibration signals produced by the accelerometers on the basis of a comparison amongst the vibration signals to determine the strongest vibration signal. Alternatively, the RFID tag in the mount 24 may transmit a vibration axis parameter (which constitutes vibration axis information), which regulates which measurement axis or combination of axes is to be used. If vibrations detected by the selected accelerometer exceed the 'trigger on' level the timer contained in the monitoring component microprocessor 52 starts. The microprocessor then operates to multiply the dose rate by the time the tool 20 is in use as measured by the timer to produce a vibration exposure value, which is added to a running total for the user for that shift.

The monitoring component 12 keeps a running total of the vibration dose for the current user and when the user is finished with that tool he removes the monitoring component and the current dosage total is recorded into monitoring component memory 54 along with the start and end times for the tool's usage. In this way a time history of vibration information seen by the monitoring component is stored in the memory 54 along with the current tool ID and employee ID. In addition, measured vibration levels (as described above) are recorded and stored.

A slow flashing green light indicates that the unit has been connected, received a valid tool ID and has sufficient battery power. The user can twist off the monitoring component 12 from its mount 24 and use it on different tools throughout the day. While the monitoring component is not in use it can be held securely on a locator/holster attached to the user's work belt.

If during tool use certain levels of cumulative HAV doses are detected visual alarms will trigger as described above. At each alarm a record will be written into memory of the time at which the user exceeded the relevant level. If during the use of each particular tool a level of vibration is detected in the monitoring component that is larger than the specified service level then the tool will be deemed to be producing too much vibration and is in need of service. At this point a visual alarm is triggered and a copy of the Tool ID written into a broken tools section in the monitoring component memory 54. The user should cut short his use of that tool and report the need for service of the tool. In addition to checking if the tool needs servicing the monitoring component records a value representing the average vibration levels seen on the tool as recorded by the accelerometer 56 and stores this in memory 54 against the tool's ID.

When the user is finished on site the monitoring component 12 is returned to an available docking bay 36 on the base component 14 and clocks out thereafter by re-swiping his user ID card 16. As soon as the monitoring component 12 is returned to a vacant docking bay 36, the base component can begin to recharge it. The monitoring component 12 knows it is in a vacant docking bay because the reed switch 58 of the monitoring component 12 is actuated by a magnetic contact in the docking bay 36. The docking bay is distinguished from a bay in a mount 24 by the monitoring component 12 performing a read of RFID tags in the vicinity. An RFID tag (such as the EM4135 from EM Microelectronic—Marin SA) provided in the docking bay responds to the reading action by modulating the RF signal with its stored data to thereby identify the base component to the monitoring component. The response also informs the monitoring component whether the base component is of a simple form (i.e. is for re-charging only and has no capability for onward communication of data) or has communication capabilities. Thereafter the base component waits for the monitoring component to download the vibration information via the RFID link. Thus the monitoring component memory is cleared for further use. Data communication between the monitoring component and the base station is via their respective RFID transceivers. The RFID transceivers are of conventional type operating according to the 125 kHz standard (such as the EM4095 from EM Microelectronic—Marin SA) or the 13.56 MHz standard (such as the EM4094 from EM Microelectronic—Marin SA). To provide for communication, the emanated field in the receiving RFID transceiver (i.e. the RFID transceiver in the base component) is turned off by writing an appropriate command word to the RFID transceiver in the case of a 125 kHz device or by writing a series of '1's after a command word containing option bits is written to the RFID transceiver in the case of a 13.56 MHz device. How this is accomplished in either case will be readily apparent to the skilled person upon reference to publicly available data sheets for the EM4095 and EM4094 devices.

Only a single RFID read/write interface is needed in the base component if there is a selectable antenna located in each docking bay 36. The information is stored on the base component on its internal memory card 18, which can store at least 3 months of data. Every month a message on the base component indicates that it is time to remove and replace the internal memory card. The replaced card 18 is sent off-site for storage on a central database provided on the Personal Computer 20. The card is read via a standard card reader connected to the PC.

Recording vibration dose information facilitates the gathering of historical information for further analysis and acts as a permanent vibration health and safety record for users. The system records the date and time of exposure and the particular tool and level of usage. This means that monitoring of and controls for users can be tighter. If necessary, action can be taken to protect personnel. Also, a central record of tools in need of service can be kept which will aid tool management and provide the means to reduce the likelihood that no user is exposed to dangerous levels of vibration from damaged equipment.

Figure 7:
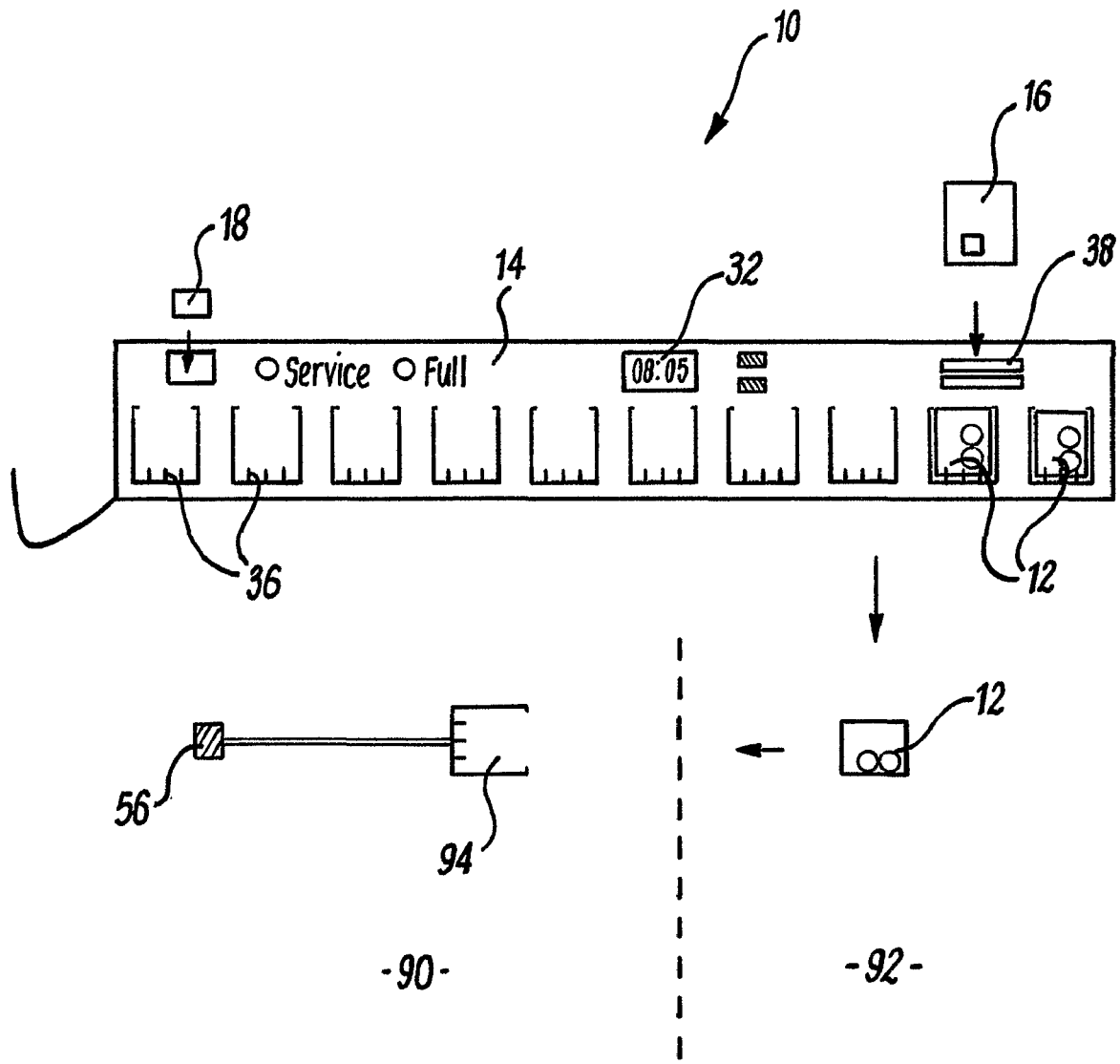
FIG. 7 is a representation of a second embodiment of the invention.

In the second embodiment of the invention represented in FIG. 7 the hand held tool monitoring apparatus 10 comprises the same components as the first embodiment. Therefore components common to drawings of the first and second embodiments have the same reference numerals. The area in FIG. 7 designated by reference numeral 90 indicates components that are fixed to the tool, e.g. the pneumatic drill 22 of FIG. 1, and the area designated by reference numeral 92 indicates a portable component. More specifically, the accelerometer is fixed to the tool and provided with a robust connector 94. The portable component is a monitoring component 12, which is the same as that of the first embodiment without the accelerometer. The monitoring apparatus of the second embodiment is operated in the same manner as the first embodiment with the notable exception of the use of the connector 94 instead of the RF link between the components that are fixed to the tool and the portable monitoring component 12.

Figure 8:
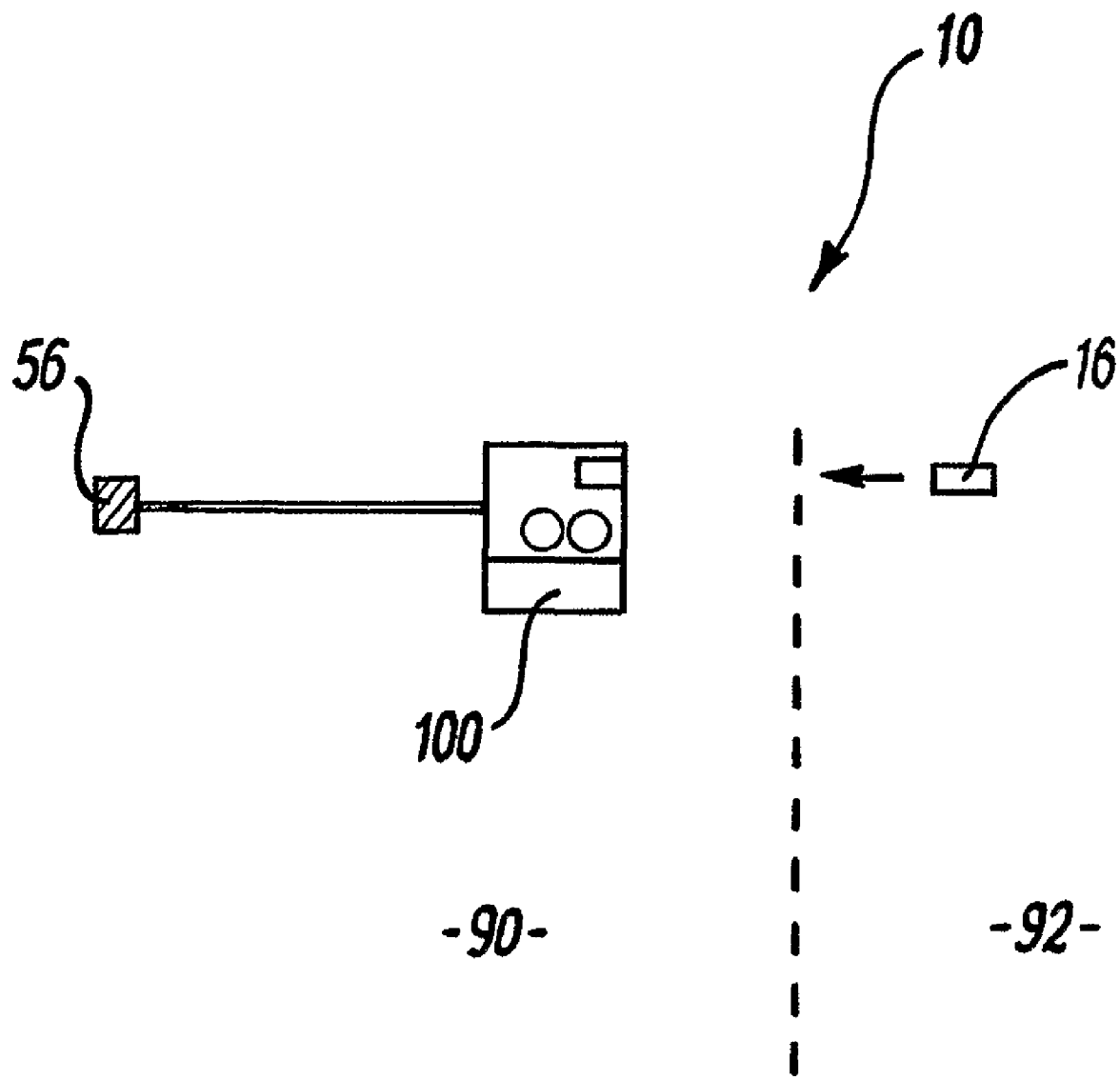
FIG. 8 is a representation of a third embodiment of the invention.

In the third embodiment of the invention represented in FIG. 8 the hand held tool monitoring apparatus 10 comprises components in common with the first embodiment that are designated by the same reference numerals. Also in common with FIG. 7, the area in FIG. 8 designated by reference numeral 90 indicates components that are fixed to the tool, e.g. the pneumatic drill 22 of FIG. 1, and the area designated by reference numeral 92 indicates a portable component. According to the third embodiment, the accelerometers 56 are attached permanently to a tool along with a processor unit 100 having a detachable rechargeable battery. The portable component is a read/write RFID based user ID card 16, which is used by a particular user in place of the magnetic strip based Employee ID in other embodiments. In use, the user inserts his RFID card 16 into the processor unit 100 upon commencing use of a tool. Vibration data is acquired by the processor unit 100 and written to the RFID card 16. Thus, it will be understood that the processor unit 100 comprises the necessary processing and interface functions present in the monitoring component 12 of the first and second embodiments. Vibration and other data is stored on a digital memory card (not shown). Recovery of stored data from the processor unit 100 is by means of a RF link (not shown) for storage in a central server, such as the Personal Computer 20 of FIG. 1. Otherwise, the third embodiment operates in the same manner as the first embodiment.

What is claimed is:
1. Hand held tool monitoring apparatus comprising a mount, which in use of the hand held monitoring apparatus forms part of a hand held tool, the mount comprising hand held tool information for the hand held tool and a communications component operable to wirelessly convey the hand held tool information to a monitoring component; and the monitoring component comprising an operative part of the hand held tool monitoring apparatus, a vibration sensor and a timer, the vibration sensor being operable to sense vibration of the hand held tool and provide a vibration signal in response to sensed vibration when the monitoring component is attached to the mount, and the timer being operative in dependence on the vibration signal to record a duration of vibration of the hand held tool, the monitoring component and the mount having respective surface profiles that are configured to engage with each other to provide for releasable attachment of the monitoring component to the mount, and the mount and monitoring component are configured to be detached from each other by a single manual operation by a user.

2. Apparatus according to claim 1, in which the mount and monitoring component are configured such that the user detaches the monitoring component from the mount solely by one of: pulling the monitoring component away from the mount; and twisting the monitoring component in relation to the mount.

3. Apparatus according to claim 1, in which one of the mount and monitoring component defines a recess configured to receive the other of the mount and the monitoring component.

4. Apparatus according to claim 1, in which the monitoring component and the mount comprise respective cooperating magnetic components that in use provide for releasable attachment of the monitoring component to the mount.

5. Apparatus according to claim 1, in which the monitoring component is configured to be carried by an operator when not in use on a hand held tool.

6. Apparatus according to claim 1, in which the mount forms an integral part of the hand held tool and in which the hand held tool and the hand held tool monitoring apparatus are configured to switch off the hand held tool when a predetermined condition is satisfied, the predetermined condition comprising at least one of: a vibration level value being reached; and an incorrect license being provided for the hand held tool monitoring apparatus.

7. Apparatus according to claim 1, in which the hand held tool information comprises hand held tool identification information.

8. Apparatus according to claim 1, in which the hand held tool information comprises a predetermined vibration dosage rate.

9. Apparatus according to claim 1, in which, where the vibration sensor is configured to be responsive to vibrations in three mutually orthogonal axes, the hand held tool information comprises vibration axis information regarding which measurement axis or combination of axes is be used for measurement or detection of vibrations.

10. Apparatus according to claim 1, in which the hand held tool monitoring apparatus further comprises a user identification component configured to identify one of a plurality of possible users, the user identification component comprising a specific user component comprising information for a specific user, the user identification component being configured to be carried by the specific user, and the monitoring apparatus comprises a separate, specific user configurable component associated with the vibration sensor to which information for the specific user can be conveyed.

11. Apparatus according to claim 1, in which the hand held tool monitoring apparatus further comprises a filter operative to change the vibration signal to take account of a change in a vibration characteristic between the hand held tool and the operator.

12. A hand held tool monitoring method using monitoring apparatus comprising a mount and a monitoring component, the method comprising the steps of: attaching the monitoring component, which comprises an operative part of the hand held tool monitoring apparatus, to the mount, the mount in use, forming part of the hand held tool and comprising hand held tool information for the hand held tool and a communications component operable to wirelessly convey the hand held tool information to the monitoring component, the monitoring component and the mount having respective surface profiles that are configured to engage with each other to provide for releasable attachment of the monitoring component to the mount, and the mount and monitoring component are configured to be detached from each other by a single manual operation by a user;

operating a vibration sensor of the hand held tool monitoring apparatus to sense a vibration of the hand held tool and to provide a vibration signal in dependence upon the sensed vibration;

operating a timer of the hand held tool monitoring apparatus in dependence upon the vibration signal to record a duration of vibration of the hand held tool; and removing the monitoring component from the mount.

13. A method according to claim 12, in which the step of attaching the mount to the hand held tool comprises attaching the mount at a location on the hand held tool spaced apart from a location where an operator engages the hand held tool when the tool is in use.

14. A method according to claim 12, in which the step of attaching the mount to the hand held tool comprises attaching the mount at a location of the hand held tool that is as close as practical to a location where the operator engages the hand held tool when the tool is in use.

15. Apparatus according to claim 1 in which the communications component is passive.

16. Apparatus according to claim 15, in which the monitoring component is operable to actuate the passive communications component and receive hand held tool information conveyed from the mount.

17. Apparatus according to claim 1 further comprising a base component configured for use at a central location spaced apart from a location of use of the vibration sensor on a hand held tool, the base component and the vibration sensor being configured for transmission of a transmission signal between the base component and the vibration sensor by at least one of a wired coupling and an inductive coupling.

18. Apparatus according to claim 1 further comprising: a base component configured for use at a central location spaced apart from a location of use of the vibration sensor on a hand held tool; and communications apparatus comprising first and second Radio Frequency Identification (RFID) transceivers, the first and second RFID transceivers being configured to wirelessly transmit data between the first and second RFID transceivers, the first RFID transceiver forming part of the base component and the second RFID transceiver forming part of the monitoring component.

* * * * *